United States Patent [19]

Balazs et al.

[11] Patent Number: 4,500,676

[45] Date of Patent: Feb. 19, 1985

[54] HYALURONATE MODIFIED POLYMERIC ARTICLES

[75] Inventors: Endre A. Balazs, Riverdale; Adolf Leshchiner, Brooklyn, both of N.Y.

[73] Assignee: Biomatrix, Inc., Ridgefield, N.J.

[21] Appl. No.: 561,816

[22] Filed: Dec. 15, 1983

[51] Int. Cl.³ ............................................. C08F 8/00
[52] U.S. Cl. ................................... 525/54.2; 424/78; 424/81; 424/82; 424/83; 524/29
[58] Field of Search ............... 525/54.2; 424/78, 81, 424/82, 83; 524/29

[56] References Cited

U.S. PATENT DOCUMENTS

| | | | |
|---|---|---|---|
| 4,272,522 | 6/1981 | Balazs | 424/94 |
| 4,349,467 | 9/1982 | Williams | 525/54.2 |
| 4,415,490 | 11/1983 | Joh | 525/54.2 |

*Primary Examiner*—Paul R. Michl
*Attorney, Agent, or Firm*—Sheldon Palmer

[57] ABSTRACT

Polymeric materials (and articles made therefrom) including polyurethanes, polyesters, polyolefins, polyamides, polysiloxanes, vinylic and acrylic polymers are rendered biocompatible by including with the polymeric material hyaluronic acid or a salt thereof. The hyaluronic acid may be coated onto the surface of the polymeric material, dispersed throughout the body of the polymeric material, or both. The hyaluronic acid on the surface of the polymeric material may optionally be cross-linked. The biocompatible polymeric materials are used in the making of various prosthetic devices including heart valves, intraocular lenses, vascular grafts, pacemaker leads and the like.

23 Claims, No Drawings

HYALURONATE MODIFIED POLYMERIC ARTICLES

BACKGROUND OF THE INVENTION

1. Field of the Invention

The present invention relates to polymeric articles modified with hyaluronic acid ("HA"), and having improved biocompatibility which enables the modified articles to be used in numerous in vivo applications, such as various prosthetic devices including artificial heart valves, vascular grafts, etc.

2. The Prior Art

Hyaluronic acid is a known, naturally occurring material which has many applications in medicine and biology. See, for example, E. A. Balazs U.S. Pat. No. 4,272,522 and publications cited therein.

SUMMARY OF THE INVENTION

The present invention is directed to polymeric articles modified with hyaluronic acid (a substance which is normally present in animal tissues) so as to confer on such articles a considerably higher degree of biocompatibility than the unmodified articles. The invention includes polymeric articles such as castings, films, fibers and fabrics which contain hyaluronic acid or salts thereof dispersed throughout the article or as a coating on the surface thereof, or both. The hyaluronic acid may also be cross-linked after preparation of the article. The thusly modified polymeric articles are therefore quite suitable for use in various prosthetic devices such as artificial heart valves, intraocular lenses, vascular grafts, pacemaker leads and the like, as well as in various kinds of drug delivery systems.

The polymers which can be modified with hyaluronic acid in accordance with the invention are quite numerous and include:

(1) polyurethanes, including aliphatic, aromatic and araliphatic polyetherurethanes and polyesterurethanes
(2) polyolefins such as polyethylene;
(3) vinyl polymers such as polyvinyl chloride, polyvinyl alcohol and polyvinyl acetate and copolymers thereof;
(4) acrylic polymers such as poly (hydroxyethyl) methacrylate and copolymers of methyl acrylate and methyl methacrylate;
(5) polyamides;
(6) polyesters; and
(7) polysiloxanes.

There are numerous methods of introducing the hyaluronic acid into a polymer or applying it onto the surface of a polymer. One method involves dissolving hyaluronic acid in an appropriate solvent and mixing the obtained solution with a polymer solution or an emulsion and thereafter forming an article, for example a film, from the mixture or applying this mixture as a coating. The suitable solvents for dissolving hyaluronic acid are water, dimethylsulfoxide and dimethylformamide. The surface of the polymeric substrate may be activated, as can the hyaluronic acid.

Another method involves adding hyaluronic acid in a solid form, preferably as a powder, to a polymer solution and thereafter forming an article, for example a film, from the obtained mixture or applying this mixture as a coating.

Still another method involves coating a particulate material with hyaluronic acid from solution and introducing the coated particles into a polymer solution and then forming an article, for example a film, from the obtained mixture or applying this mixture as a coating. Examples of suitable particulate materials are ion exchange resins, silica, alumina, etc.

Finally, in any of the methods described above, the hyaluronic acid can be cross-linked before or after mixing with the polymer with the use of various cross-linking agents.

DETAILED DESCRIPTION OF THE INVENTION

The following examples (wherein all parts given are by weight unless otherwise specified) illustrate the several embodiments of the invention, without however being a limitation thereof, the invention being solely defined by the claims.

In Examples 1–4, improved polyurethane articles were prepared which consist of a layer of polyurethane and one or two layers of an elastic film-forming mixture of hyaluronic acid with another polymer or polymers.

EXAMPLE 1

A piece of polyetherurethane rubber film (Upjohn) was activated by dipping in a dimethylformamide bath for 10 seconds and following washing with a water/acetone mixture of 1:30 by volume for one minute and then with water for one minute.

A mixture containing hyaluronic acid was prepared in the following manner: 31.0 g of a 1% water solution of the sodium salt of hyaluronic acid (prepared from rooster combs, protein content 1.15%, intrinsic viscosity [n] 2,700) was diluted with 60.0 g of water and then mixed with 6.7 g of an aliphatic polyurethane water emulsion (Neo Rez R962, Polyvinyl Chemical Industries). A translucent, moderately viscous mixture was obtained, solid content 2.96%, hyaluronic acid/polyurethane ratio was about 1:4. The activated polyurethane film was dipped into the prepared mixture, then dried in air for 30 minutes and, finally, in a vacuum oven at 55° C. and 43 mm Hg for 30 minutes. The obtained article consisted of a layer of the polyetherurethane rubber film coated from both sides with a continuous film consisting of the aliphatic polyurethane and sodium hyaluronate.

EXAMPLE 2

The procedure described in Example 1 was repeated with the exception that 0.3 g of a polyfunctional aziridine compound (Polyvinyl Chemical Industries, cross-linker CX-100) was added. The obtained article consisted of a layer of the polyetherurethane rubber film coated from both sides with a continuous film consisting of an aliphatic polyetherurethane and cross-linked sodium hyaluronate.

EXAMPLE 3

A glass rod was coated by dipping it into a 10% solution of a polyetherurethane (The Upjohn Company, Pellethane 80 AE) in dimethylformamide. The polymer film was coagulated in water/acetone mixture of 3:1 by volume. The film on the rod was dried in an oven at 80° C. for 30 minutes. The second layer was applied by dipping into the polyurethane-sodium hyaluronate mixture according to Example 1.

The obtained tubular article consisted of two layers, one of which was a polyetherurethane film and the second one a mixed film from an aliphatic polyurethane and cross-linked sodium hyaluronate.

EXAMPLE 4

1.09 g of air dried sodium hyaluronate was dissolved in a mixture of 4.40 g of water and 67 g of dimethylformamide. 10 g of the resulting solution were mixed with 10 g of a 25% solution of a polyetherurethane (Upjohn Company, Pellethane 80 AE) in dimethylacetamide. Solid content in this solution was 13.66% with sodium hyaluronate/polyurethane ratio of 1:40. A glass rod was dipped into this viscous solution. The polymers were coagulated in a water/acetone=3:1 by volume mixture. The tubular film was washed in water 10 minutes and then dried off in a vacuum oven at 45 mm Hg and 50° C. for 45 minutes.

The following examples illustrate the application of a hyaluronic acid coating onto a polyester fabric (Example 5) and onto a PVC film (Example 6)

EXAMPLE 5

A solution containing 1.5% by weight of hyaluronic acid and 1.0% by weight of cross-linking agent CX-100 was prepared. A piece of Dacron knitted fabric was dipped into the solution for 2 minutes. The excess of the solution was squeezed off and the sample was dried overnight. The hyaluronic acid content in the coated fabric was 3.7% by weight.

EXAMPLE 6

A water solution of sodium hyaluronate was added to a vinyl acrylic water emulsion (Amsco-Res 9205, Union Chemicals Division) to obtain a mixture containing 0.25% by weight of hyaluronic acid. The mixture was applied by dipping onto polyvinyl chloride (PVC) film and dried in air for 2 hours. The coated film was treated in 1% by weight solution of cross-linking agent CX-100 in a water-acetone mixture containing 20% by volume of acetone and dried in air for 3 hours. A film with a well adhered coating containing hyaluronic acid was obtained.

The following examples illustrate another approach to obtaining a polyurethane film containing sodium hyaluronate, namely, introducing sodium hyaluronate in a finely divided powder form into a polyurethane solution (followed by casting the mixture) and precipitating the film by the appropriate coagulating medium.

EXAMPLE 7

Sodium hyaluronate (0.33 g; intrinsic viscosity 3,160) in a finely divided powder form was added to 10.69 g of polyurethane (Pellethane 80AE, Upjohn Company) solution in dimethylacetamide (concentration 16.4% by weight). The mixture was spread on a glass plate with the aid of a glass rod and put into 100 ml of 95% ethyl alcohol. The precipitated, milky-white film was left in the alcohol for 10 minutes, then removed from the bath, washed twice with ethanol and dried in air. The obtained elastic film contained 9.35% by weight sodium hyaluronate.

The following example illustrates the modification of the film obtained as described above in Example 7 which leads to the formation of a cross-linked hyaluronic acid layer on the surface of the film. The treatment consists in putting the film into a water solution of the cross-linking agent which cross-links hyaluronic acid upon drying. In this treatment, hyaluronic acid particles swell and partially dissolve in water and migrate to the surface of the film. As a result, there is a layer of a concentrated hyaluronic acid solution on the surface. Upon drying, hyaluronic acid is cross-linked by the cross-linking agent and, in this way, a layer of cross-linked hyaluronic acid is formed on the film surface.

EXAMPLE 8

The film obtained in Example 7 was dipped into a solution of polyfunctional arizidine compound in water (0.5% by weight; cross-linker, CX-100, Polyvinyl Chemical Industries) for 1 minute, then removed from the solution and dried in air for 2 hours. Then the film was washed repeatedly in water and dried. The film obtained had a continuous layer of cross-linked hyaluronic acid on its surface which was proven by staining the film in a water solution of Toluidine On Blue.

The following example illustrates a variant of the approach described above. In this variant, a material consisting of small particles, e.g., ion exchange resin, silica, alumina, etc., is coated with hyaluronic acid, and these coated particles are introduced into a polyurethane.

EXAMPLE 9

An ion exchange resin (5.0 g of Dowex 50W-2x, mesh size 200–400) was mixed with 10.6 g of hyaluronic acid in water at a concentration 7.2 mg/ml. The mixture was dried in a vacuum oven. The product obtained contained 1.5% hyaluronic acid. The coated resin (0.5 g) was mixed with 5 g of the polyurethane solution used in the preceding example. The film was precipitated and treated as above. The hyaluronic acid content in the film was 0.38%.

The following example illustrates modification of the surface properties of silicone rubber with a hyaluronate containing coating.

EXAMPLE 10

A piece of a silicone rubber (Silastic, Dow Corning) was dipped into a 10% solution of an amine-containing silane (Silane A-1100, Union Carbide) in toluene, dried 10 minutes in air and then in an oven at 60° C. for 10 minutes. Thus treated rubber was dipped into a solution containing 0.5% of sodium hyaluronate and 0.12% of cross-linker CX-100. The sample was dried in air and then in an oven at 70° C. for 10 minutes. The modified sample had a wettable surface. This property was permanent as was found by repeatedly washing the sample with water.

The biocompatibility of the preparations according to the invention was demonstrated by the test hereafter described.

EXAMPLE 11—BLOOD COMPATIBILITY TEST

Release of $^3$H-serotonin by human platelets was used in preliminary studies to assess the blood reactivity of the product of Example 5. Normal human venous blood was drawn into plastic syringes and immediately transferred to plastic tubes containing 3.8% sodium citrate (one part citrate to nine parts whole blood). Platelet rich plasma was prepared by centrifugation at 4° C. for 15 minutes at 125×g and removed by serological pipet to a plastic or siliconized test tube. $^3$H-serotonin ($^3$H-5-hydroxytryptamine, $^3$H-5HT; New England Nuclear, 26.3 Ci/mmol, 1 mCi/ml ethanol-water) was added to platelet rich plasma (PRP), 0.2–0.5 ul/ml PRP, and incubated for 15 minutes at 37° C. In the assay, siliconized or polypropylene test tubes were used; thrombin was used as a positive control, coated and uncoated samples were tested. 1.0-2.0 ml of $^3$H-5HT-PRP was added to each of duplicate tubes containing samples to be assayed: a 50 ul aliquot was removed from the control mixture for determination of total radioactivity. Following the appropriate incubation period (10-120 minutes) 0.2-0.5 ml aliquots of the suspension were removed and centrifuged over silicon oil in an Eppendorf microfuge for two minutes at 12,000×g. 50 ul of the supernatant was removed from each tube, mixed with 5 ml of liquid scintillation fluid, and radioactivity measured by beta-spectrometry. The amount of $^3$H-5HT released by thrombin or the test samples was the increment in radioactivity of the supernatant (radioactivity of experimental samples minus radioactivity control). Coated samples of the product of example 5 were consistently less reactive in terms of amount of $^3$H-5HT released; uncoated samples induced 52% greater release than the coated samples.

Variations and modifications can, of course, be made without departing from the spirit and scope of the invention.

Having thus described our invention what we desire to secure by Letters Patent and hereby claim is:

1. A composition of matter comprising a polymeric material modified by the inclusion therein of hyaluronic acid or a salt thereof.

2. A composition according to claim 1 wherein the polymeric material is a polyurethane, polyolefin, a vinylic polymer or copolymer, an acrylic polymer or copolymer, a polyamide, a polyester or a polysiloxane.

3. A composition according to claim 2 wherein the polymeric material is a polyurethane.

4. A composition according to claim 3 wherein the polyurethane is an aliphatic, aromatic or araliphatic polyetherurethane or polyesterurethane.

5. A composition according to claim 3 wherein the included hyaluronic acid or salt thereof is coated onto the surface of the polymeric material.

6. A composition according to claim 3 wherein the included hyaluronic acid is covalently bonded to the surface of the polymeric material.

7. A composition according to claim 3 wherein the hyaluronic acid is distributed throughout the body and on the surface of the polymeric material.

8. A composition according to claim 5 wherein the hyaluronic acid on the surface of the polymeric material is cross-linked.

9. A composition according to claim 6 wherein the hyaluronic acid on the surface of the polymeric material is cross-linked.

10. A composition according to claim 7 wherein the hyaluronic acid on the surface of the polymeric material is cross-linked.

11. A formed article made from the composition according to claim 3.

12. An article according to claim 11 which is a casting, a film, a fiber or a fabric.

13. A composition according to claim 2 wherein the polymeric material is a polyester.

14. A composition according to claim 13 wherein the included hyaluronic acid or salt thereof is coated onto the surface of the polymeric material.

15. A composition according to claim 14 wherein the hyaluronic acid on the surface of the polymeric material is cross-linked.

16. A formed article made from the composition according to claim 13.

17. An article according to claim 16 which is a casting, a film, a fiber or a fabric.

18. A composition according to claim 2 wherein the polymeric material is a vinylic polymer.

19. A composition according to claim 18 wherein the vinylic polymer is a polyvinyl chloride.

20. A composition according to claim 19 wherein the included hyaluronic acid or salt thereof is coated onto the surface of the polymeric material.

21. A composition according to claim 20 wherein the hyaluronic acid on the surface of the polymeric material is cross-linked.

22. A formed article made from the composition according to claim 18.

23. An article according to claim 22 which is a casting, a film, a fiber or a fabric.

* * * * *